(12) United States Patent
Wang et al.

(10) Patent No.: US 9,616,199 B2
(45) Date of Patent: Apr. 11, 2017

(54) IRRIGATED CATHETER EMPLOYING MULTI-LUMENAL IRRIGATION TUBING

(75) Inventors: Huisun Wang, Maple Grove, MN (US); Dale E. Just, Minneapolis, MN (US); Harry A. Puryear, Shoreview, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 2075 days.

(21) Appl. No.: 12/650,956

(22) Filed: Dec. 31, 2009

(65) Prior Publication Data

US 2011/0160721 A1   Jun. 30, 2011

(51) Int. Cl.
| | | |
|---|---|---|
| A61B 18/14 | (2006.01) | |
| A61M 25/00 | (2006.01) | |
| A61B 18/00 | (2006.01) | |

(52) U.S. Cl.
CPC ....... *A61M 25/007* (2013.01); *A61B 18/1492* (2013.01); *A61M 25/003* (2013.01); *A61M 25/0009* (2013.01); *A61B 2018/00214* (2013.01); *A61B 2218/002* (2013.01); *A61M 25/0071* (2013.01); *A61M 2025/0037* (2013.01); *Y10T 29/49826* (2015.01)

(58) Field of Classification Search
CPC .......... A61B 18/1492; A61B 2218/002; A61B 2018/00214; A61M 25/003; A61M 25/007; A61M 25/0009; A61M 25/0071
USPC ............... 606/41, 45–50; 604/19–22, 39–45; 607/115, 119, 122
See application file for complete search history.

(56) References Cited

U.S. PATENT DOCUMENTS

RE31,873 E   *   4/1985   Howes ............... A61B 5/02152
                                                                600/487
4,619,643 A   *   10/1986   Bai ..................... A61M 5/1582
                                                                604/170.03

(Continued)

FOREIGN PATENT DOCUMENTS

| JP | 2001340466 | 11/2001 |
|---|---|---|
| JP | 2009261767 | 11/2009 |

(Continued)

OTHER PUBLICATIONS

International Search Report and Written Opinion of the International Searching Authority for PCT/US2010/049832 dated Nov. 9, 2010.

*Primary Examiner* — Linda Dvorak
*Assistant Examiner* — Samantha Good
(74) *Attorney, Agent, or Firm* — Wiley Rein LLP

(57) ABSTRACT

An irrigated catheter includes a catheter body having both proximal and distal irrigation passageways. A first fluid delivery tube feeds the proximal irrigation passageway and is fluidly isolated from the distal irrigation passageway, while a second fluid delivery tube feeds the distal irrigation passageway and is fluidly isolated from the proximal irrigation passageway. Typically, the first and second fluid delivery tubes will be unitary, at least through the catheter body. The overall shape of the first and second fluid delivery tubes, as well as their respective lumens, may vary as necessary for a particular application of the irrigated catheter. The system also includes an irrigation fluid source and at least one pump to deliver the irrigation fluid through the irrigation passageways. Typically, the pump will be a volume-driven pump, such as a rolling pump.

7 Claims, 4 Drawing Sheets

(56) References Cited

U.S. PATENT DOCUMENTS

| | | | |
|---|---|---|---|
| 5,378,230 A * | 1/1995 | Mahurkar | A61M 25/0023 604/264 |
| 6,569,159 B1 * | 5/2003 | Edwards et al. | 606/41 |
| 2003/0109915 A1 | 6/2003 | Don Michael | |
| 2005/0177151 A1 * | 8/2005 | Coen et al. | 606/41 |
| 2007/0270791 A1 * | 11/2007 | Wang et al. | 606/41 |
| 2008/0249522 A1 | 10/2008 | Pappone et al. | |
| 2009/0125016 A1 | 5/2009 | Wang et al. | |
| 2009/0163912 A1 | 6/2009 | Wang et al. | |

FOREIGN PATENT DOCUMENTS

| | | |
|---|---|---|
| WO | 0041761 | 7/2000 |
| WO | 03045464 | 6/2003 |
| WO | 2007018963 | 2/2007 |
| WO | 2007136979 | 11/2007 |

* cited by examiner

IRRIGATED CATHETER EMPLOYING MULTI-LUMENAL IRRIGATION TUBING

BACKGROUND OF THE INVENTION a. Field of the Invention

The instant invention relates to catheters that are used in the human body. In particular, the instant invention relates to an irrigated catheter utilizing multi-lumenal irrigation tubing to provide multiple dedicated and/or independent irrigation flows. The present invention also relates to methods of manufacturing and using such a catheter.

b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site, for example a site within the patient's heart.

A typical electrophysiology catheter includes an elongate shaft and one or more electrodes on the distal end of the shaft. The electrodes may be used for ablation, diagnosis, or the like. Electrophysiology catheters also often include irrigation, for example, to provide a conduction pathway to carry ablative energy to nearby tissue and/or to cool nearby tissue to prevent excessive thermal damage such as charring.

Extant irrigated catheters often exhibit certain disadvantages. For example, in an irrigated catheter that includes a pressure-driven irrigation flow, if an irrigation passageway becomes obstructed, the irrigation fluid will seek lower pressure outlets and redistribute to other irrigation passageways, leading to a situation where certain areas of the catheter are not irrigated to the extent desired. As another example, in an irrigated catheter that includes a volume-driven irrigation flow, if an irrigation passageway becomes plugged, the volume-driven pump will push to open the passageway (that is, the same volume of irrigation fluid will be delivered to the occluded passageway, regardless of the pressure necessary to do so).

These shortcomings may be ameliorated by creating multiple independent irrigation flows. This solution, however, presents its own shortcomings. One way in which multiple independent irrigation flows is to employ multiple saline bags, with one bag dedicated to each irrigation flow. Saline bags, however, are not ideal for delivering accurate, consistent, and predictable irrigation flows. To overcome these disadvantages associated with saline bags, an irrigation or infusion pump may be employed, but it is not economical to utilize multiple such pumps to provide multiple irrigation flows.

BRIEF SUMMARY OF THE INVENTION

It is therefore an object of the present invention to provide an irrigated catheter having multiple dedicated and/or independent irrigation flows.

It is another object of the present invention to provide an irrigated catheter having multiple dedicated and/or independent irrigation flows without requiring multiple irrigation sources.

Yet another object of the present invention is to provide an irrigated catheter having multiple dedicated and/or independent irrigation flows driven by a single irrigation pump.

Disclosed herein is an irrigated catheter system, including: a catheter body having at least one proximal irrigation passageway and at least one distal irrigation passageway; a first fluid delivery tube extending through the catheter body and defining a first irrigation lumen, wherein the first irrigation lumen is in fluid communication with the at least one proximal irrigation passageway and fluidly isolated from the at least one distal irrigation passageway; and a second fluid delivery tube extending through the catheter body and defining a second irrigation lumen, wherein the second irrigation lumen is in fluid communication with the at least one distal irrigation passageway and fluidly isolated from the at least one proximal irrigation passageway. Advantageously, the first fluid delivery tube is attached to the second fluid delivery tube to form a unitary double-lumen fluid delivery tube that, in some aspects of the invention, has an oval-shaped axial cross-section. It is also contemplated that the first irrigation lumen and the second irrigation lumen may have substantially congruent axial cross-sectional shapes. Optionally, the first fluid delivery tube is integrally formed with the second fluid delivery tube, though the first and second fluid delivery tubes may also be separately formed and joined via the application of heat, adhesives, or any other suitable method.

In certain embodiments, the irrigated catheter system also includes a proximal fluid manifold and a distal fluid manifold. The first irrigation lumen may then be in fluid communication with the at least one proximal irrigation passageway via the proximal fluid manifold, while the second irrigation lumen may be in fluid communication with the at least one distal irrigation passageway via the distal fluid manifold. Optionally, the second irrigation lumen may be in fluid communication with the at least one distal irrigation passageway via a distal fluid delivery passageway.

The irrigated catheter system may also include at least one irrigation fluid source fluidly connected to the first fluid delivery tube and the second fluid delivery tube and at least one pump operable to pump an irrigation fluid from the at least one irrigation fluid source, through the first fluid delivery tube and the second fluid delivery tube, and out the at least one proximal irrigation passageway and the at least one distal irrigation passageway. It is contemplated that a single irrigation fluid source may be fluidly connected to both the first and second fluid delivery tubes. Alternatively, a first irrigation fluid source may be fluidly connected to the first fluid delivery tube, and a second irrigation fluid source may be fluidly connected to the second fluid delivery tube. The at least one pump is desirably a volume-driven pump, such as a rolling pump.

Also disclosed herein is an irrigated electrophysiology catheter, including: a catheter shaft having a proximal end portion and a distal end portion, the distal portion including a plurality of irrigation passageways; at least one electrode on the distal end portion of the catheter shaft; and a multi-lumenal fluid delivery tube extending from the proximal end portion of the catheter shaft and through the catheter shaft, wherein the multi-lumenal fluid delivery tube defines a plurality of separate fluid delivery lumens including a first fluid delivery lumen and a second fluid delivery lumen, wherein the first fluid delivery lumen is in fluid communication with a first subset of the plurality of irrigation passageways and fluidly isolated from a second subset of the plurality of irrigation passageways; and wherein the second fluid delivery lumen is in fluid communication with a third subset of the plurality of irrigation passageways and fluidly isolated from a fourth subset of the plurality of irrigation passageways. Typically, the first subset of the plurality of irrigation passageways is co-extensive with the fourth subset of the plurality of irrigation passageways and the second subset of the plurality of irrigation passageways is co-extensive with the third subset of the plurality of irrigation passageways. The multi-lumenal fluid delivery tube may have a flattened axial cross-sectional shape. Each of the plurality of separate fluid delivery lumens defined by the multi-lumenal fluid delivery tube may have a substantially identical axial cross-sectional area.

The irrigated electrophysiology catheter may also include a first irrigation manifold in fluid communication with both the first fluid delivery lumen and the first subset of the plurality of irrigation passageways and a second irrigation manifold in fluid communication with both the second fluid delivery lumen and the third subset of the plurality of irrigation passageways. Desirably, the first irrigation manifold is fluidly isolated from the second irrigation manifold.

The irrigated electrophysiology catheter may also include at least one irrigation fluid supply in fluid communication with the first fluid delivery lumen and the second fluid delivery lumen and a pump operable to pump an irrigation fluid from the at least one irrigation fluid supply, through the first fluid delivery lumen and the second fluid delivery lumen, and out the plurality of irrigation passageways. In some aspects of the invention, the irrigated electrophysiology catheter also includes a generator operably coupled to the at least one electrode.

The present invention also provides a method of manufacturing an irrigated catheter assembly that includes the steps of: providing a catheter body including a plurality of irrigation passageways; providing a first fluid delivery tube defining a first irrigation lumen; providing a second fluid delivery tube defining a second irrigation lumen; inserting the first fluid delivery tube into the catheter body; fluidly coupling the first irrigation lumen to a first subset of the plurality of irrigation passageways; fluidly isolating the first irrigation lumen from a second subset of the plurality of irrigation passageways; inserting the second fluid delivery tube into the catheter body; fluidly coupling the second irrigation lumen to a third subset of the plurality of irrigation passageways; and fluidly isolating the second irrigation lumen from a fourth subset of the plurality of irrigation passageways. The first and second fluid delivery tubes may be provided as an integrally formed, multi-lumenal fluid delivery tube defining both the first irrigation lumen and the second irrigation lumen. Alternatively, the first and second fluid delivery tubes may be formed and provided separately and attached to each other via the application of heat, adhesive, or another suitable method.

An advantage of an irrigated catheter according to the present invention is that it includes multiple dedicated and/or independent irrigation flows.

Another advantage of an irrigated catheter according to the present invention is that the multiple dedicated and/or independent irrigation flows may be provided by a single irrigation source.

Still another advantage of the present invention is that the multiple dedicated and/or independent irrigation flows may be driven by a single pump.

The foregoing and other aspects, features, details, utilities, and advantages of the present invention will be apparent from reading the following description and claims, and from reviewing the accompanying drawings.

DETAILED DESCRIPTION OF THE INVENTION

The present invention provides a multi-lumenal irrigation tubing that is desirably and advantageously adapted to deliver multiple dedicated and/or independent irrigation flows. It also provides an irrigated catheter or catheter system, such as an irrigated ablation or electrophysiology mapping catheter, employing such tubing, and optionally a rolling pump, to provide dedicated and/or independent irrigation flows to a distal end portion of such catheter.

For purposes of description, the present invention will be described and illustrated in connection with an irrigated radiofrequency ("RF") ablation catheter. Reference will also be made to an irrigated electrophysiology mapping catheter. Both are described with reference to dedicated distal and proximal irrigation flows. It is contemplated, however, that the described features and methods may be incorporated into any number of catheters or other diagnostic and/or therapeutic devices having any number of irrigation passageways, as would be appreciated by one of ordinary skill in the art. Indeed, the present teachings may be employed to good advantage in any irrigated catheter or similar device where it is advantageous or desirable to have spaced-apart irrigation ports provided with dedicated and/or independent irrigation flows.

Irrigated Catheter Systems

Figure 1:
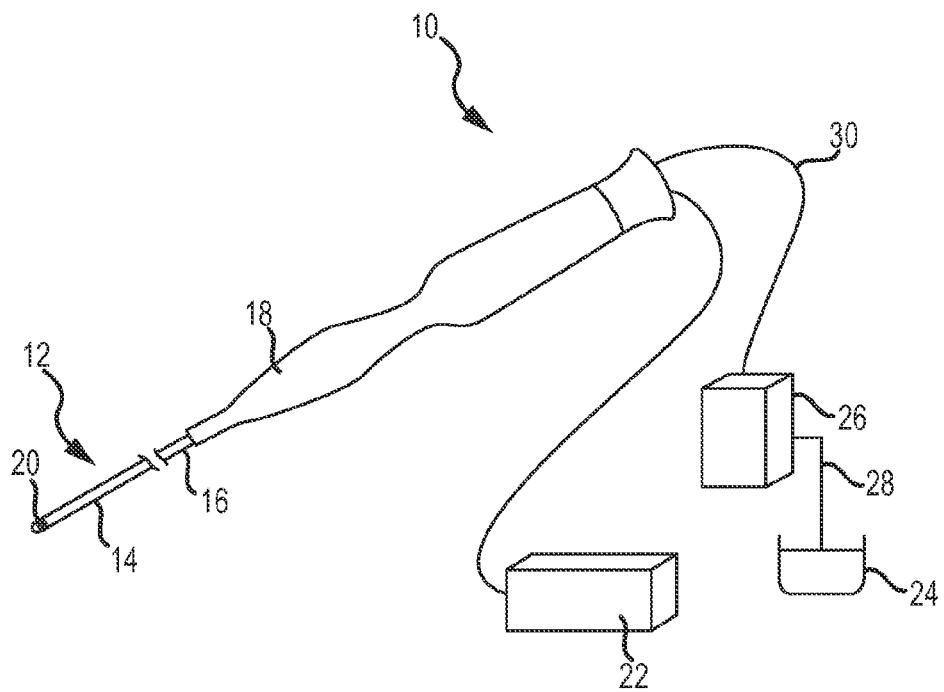
FIG. 1 is a schematic illustration of an irrigated ablation catheter system.

Referring now to the figures, and in particular to FIG. 1, an ablation catheter system 10 includes an elongate catheter body or shaft 12 having a distal end portion 14 and a proximal end portion 16. Catheter body 12 is typically flexible and of sufficient length to be navigable through the tortuous paths of a patient's vasculature to an intended destination for diagnosis and/or therapy, such as introduction into a particular chamber of the patient's heart in order to ablate cardiac tissue during treatment of cardiac arrhythmia. In furtherance of this objective, a handle 18 may be coupled to proximal end 16 of catheter body 12 to control catheter 10. Handle 18 may include one or more suitable actuators (not shown) to deflect or steer distal end portion 14 as it navigates the vasculature en route to the intended destination.

One or more electrodes 20 are provided on distal end portion 14 of catheter body 12. Electrodes 20 are operably connected to a generator 22, such as a radiofrequency ("RF") generator, in order to energize electrodes 20 for diagnostic (e.g., mapping) or therapeutic (e.g., ablation or pacing) purposes.

Figure 6:
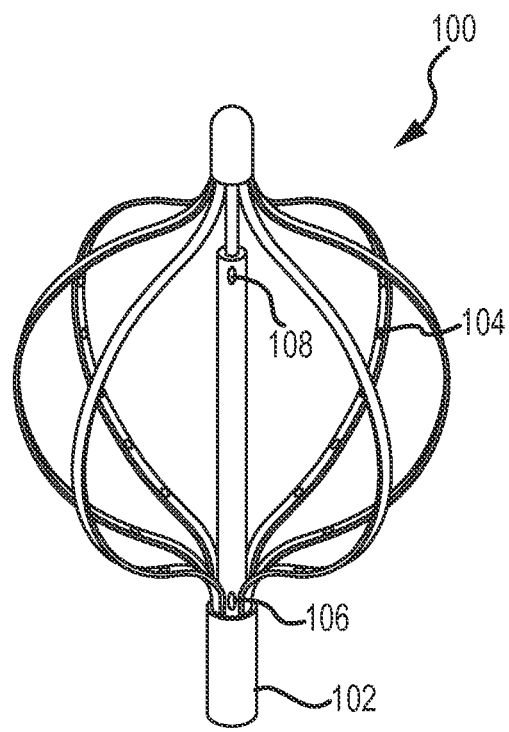
FIG. 6 depicts an electrophysiology mapping catheter including dedicated proximal and distal irrigation passageways.

FIG. 6 depicts the distal end region 100 of an electrophysiology mapping catheter 102. As shown in FIG. 6, distal end region 100 of electrophysiology mapping catheter 102 includes a plurality of electrodes 104, which may be adapted for contact and/or non-contact electrophysiology studies of an anatomical region (e.g., a heart chamber). Also visible are proximal irrigation port 106 and distal irrigation port 108, both of which may be supplied with irrigation fluid as discussed in greater detail below.

The ordinarily skilled artisan will be familiar with the general components of ablation catheter system 10 and electrophysiology mapping catheter 102 discussed above. Thus, they are not described in further detail herein, except as may be necessary to understand the specifics of the present invention.

Irrigation fluid is provided via at least one irrigation fluid source 24, such as a saline reservoir, and delivered via at least one pump 26. Supply tubing 28 connects pump 26 to irrigation fluid source 24, while multi-lumenal tubing 30, several embodiments of which are discussed in further detail below, connects pump 26 to catheter body 12. Pump 26, which will typically be a volume-driven pump, such as a rolling pump, is operable to pump an irrigation fluid from irrigation fluid source 24, through supply tubing 28, and then through multi-lumenal tubing 30, to deliver irrigation fluid to distal end portion 14 of catheter body 12. Desirably, only a single pump 26 is used, as this increases the economy and reduces the complexity of ablation catheter system 10.

It should be understood that irrigation fluid may also be delivered to distal end portion 14 of catheter body 12 via gravity (e.g., via a saline bag fitted with an appropriate valve). Likewise, irrigation fluid may be delivered via a combination of a positive displacement device (e.g., a volume- or pressure-driven pump) and via gravity.

Multi-Lumenal Tubing

Figure 2A:
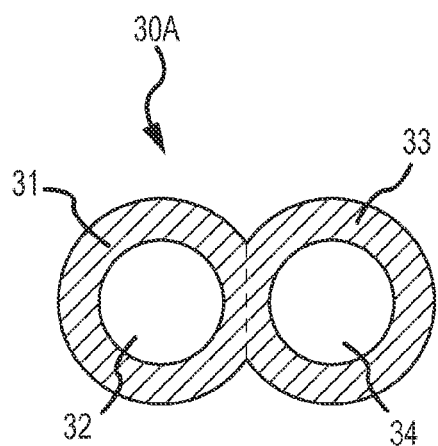
FIG. 2A is an axial cross-sectional view of one embodiment of a multi-lumenal tubing having two lumens of substantially identical cross-sectional configuration.

FIG. 2A depicts an axial cross-section of a first embodiment of multi-lumenal tubing 30 denoted 30A. Specifically, FIG. 2A depicts an embodiment where the multi-lumenal tubing includes two conjoined fluid delivery tubes 31 and 33, with a hypothetical boundary between fluid delivery tubes 31 and 33 shown in dashed line. Fluid delivery tubes 31 and 33 respectively define two fluid delivery lumens (also referred to herein as "irrigation lumens"): first fluid delivery lumen 32 and second fluid delivery lumen 34. In the embodiment shown in FIG. 2A, first fluid delivery lumen 32 and second fluid delivery lumen 34 have substantially identical axial cross-sectional areas. That is, first fluid delivery lumen 32 and second fluid delivery lumen 34 are substantially congruent, having the same size (e.g., the same diameter) and the same shape (e.g., substantially circular).

Figure 2B:
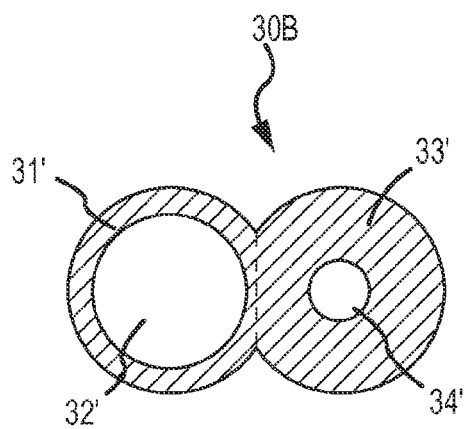
FIG. 2B is an axial cross-sectional view of another embodiment of a multi-lumenal tubing having two lumens of differing size.

FIG. 2B depicts an axial cross-section of a second embodiment of multi-lumenal tubing 30 denoted 30B. Specifically, FIG. 2B depicts an embodiment where the multi-lumenal tubing includes two conjoined fluid delivery tubes 31' and 33', respectively defining a first fluid delivery lumen 32' and a second fluid delivery lumen 34'. As with FIG. 2A, a hypothetical boundary between delivery tubes 31' and 33' is shown in dashed line. In contrast to the embodiment of FIG. 2A, however, fluid delivery lumens 32' and 34' have different axial cross-sectional areas (e.g., they are different sizes).

Figure 3:
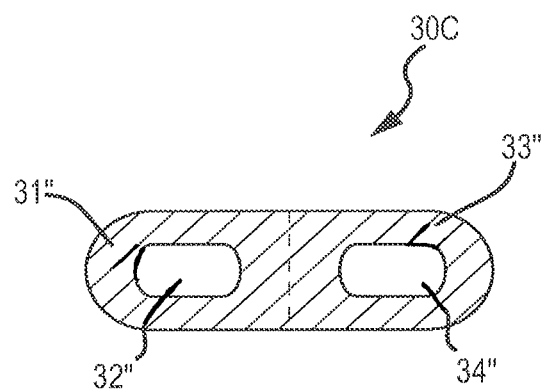
FIG. 3 is an axial cross-sectional view of still another embodiment of a multi-lumenal tubing having a flattened, or racetrack shaped, axial cross-sectional configuration.

FIGS. 2A and 2B depict multi-lumenal tubing 30 that has, overall, an axial cross-sectional shape resembling a "figure eight" due to the joining of two substantially circular tubing members. Alternatively, as shown in FIG. 3, multi-lumenal tubing 30, denoted as 30C, may have an oval (or otherwise flattened) axial cross-sectional shape. Of course, as also shown in FIG. 3, the fluid delivery lumens 32" and 34", defined respectively by fluid delivery tubes 31" and 33", may also have a flattened axial cross-sectional shape.

Figure 7:
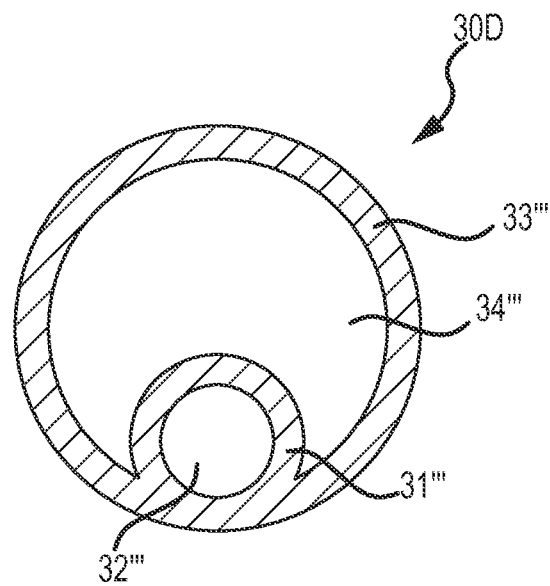
FIG. 7 illustrates an axial cross-sectional view of a multi-lumenal tubing according to certain aspects of the present invention.

It is also contemplated that multi-lumenal tubing 30 may have nested lumens, coaxial or otherwise, such as depicted in FIG. 7. For example, multi-lumenal tubing 30D, depicted in FIG. 7, may have a first fluid delivery lumen 32' defined by a first fluid delivery tube 31' located within a second fluid delivery lumen 34''' defined by a second fluid delivery tube 33'''. As explained in further detail below, first fluid delivery lumen 32''' may deliver an irrigation fluid to more proximal irrigation passageways, while second fluid delivery lumen 34' may deliver an irrigation fluid to more distal irrigation passageways.

One of ordinary skill in the art will appreciate that multi-lumenal tubing 30 may take any suitable overall shape (e.g., figure eight, as shown in FIGS. 2A and 2B, flattened/race-track shaped, as shown in FIG. 3, or nested, as shown in FIG. 7). Likewise, fluid delivery lumens 32 and 34 may take any suitable shape (e.g., circular, elliptical). Similarly, the fluid delivery lumens may have the same axial cross-sectional configuration (e.g., shape and size), or may differ in size and/or shape. In other words, the overall configuration of multi-lumenal tubing 30, as well as the number, size, and configuration of the lumens defined thereby, may vary and can be readily tailored to a particular application of catheter system 10.

As shown in FIGS. 2A, 2B, 3, and 7, multi-lumenal tubing 30 is a unitary tubing that defines a plurality of irrigation lumens. This unitary tubing may be formed integrally (e.g., by extruding a tube with multiple lumens in a single manufacturing step). Alternatively, unitary multi-lumenal tubing 30 may be formed by joining separately-formed tubes, each having one or more lumens, to each other via the application of heat, adhesives, or via another suitable bonding technique. It should also be appreciated that multi-lumenal tubing 30 need not be unitary along its entire length, though it will typically be unitary at least throughout the length of catheter body 12. For example, the proximal end of multi-lumenal tubing 30 may have fluid delivery tubes 31 and 33 separated from each other, such that multi-lumenal tubing 30 has a Y-shape, allowing for connection of fluid delivery lumens 32 and 34 to disparate fluid supplies. Conventional medical tubing materials, such as PVC, polyurethane, and other polymeric materials, are suitable for multi-lumenal tubing 30.

Dedicated Irrigation Passageways

Figure 4:
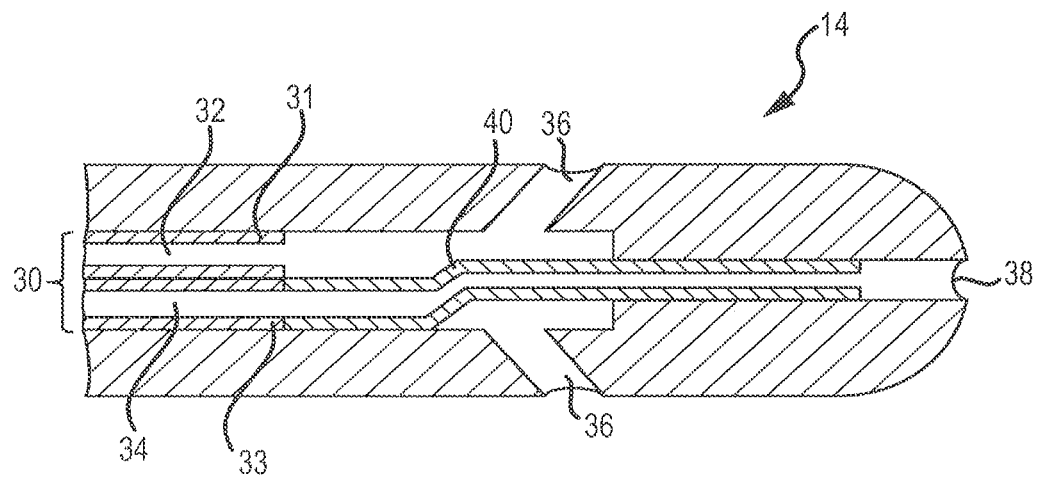
FIG. 4 is a longitudinal cross-sectional view of the distal end portion of a catheter body according to some aspects of the present invention.

FIG. 4 depicts a cut-away view depicting the interior of a first embodiment of distal end portion 14 of catheter body 12. Of course, this configuration may also be employed in distal end region 100 of electrophysiology mapping catheter 102 (or any other irrigated catheter or similar device) to deliver dedicated proximal and distal irrigation flows. As shown in FIG. 4, distal end portion 14 of catheter body 12 includes a plurality of irrigation passageways, including at least one proximal irrigation passageway 36 and at least one distal irrigation passageway 38. Though only two proximal irrigation passageways 36 and one distal irrigation passageway 38 are depicted, any number of irrigation passageways are regarded as within the spirit and scope of the present teachings. As discussed in greater detail below, however, each irrigation lumen of multi-lumenal tubing 30 is fluidly coupled to some of the irrigation passageways while being fluidly isolated from other irrigation passageways. Likewise, proximal irrigation passageways 36 are fluidly isolated from distal irrigation passageway 38.

As seen in FIG. 4, multi-lumenal tubing 30 (e.g., first fluid delivery tube 31 and second fluid delivery tube 33) extends through catheter body 12. First irrigation lumen 32 is in fluid communication with proximal irrigation passageway 36, while second irrigation lumen 34 is in fluid communication with distal irrigation passageway 38. In some embodiments of the invention, second irrigation lumen 34 is in fluid communication with distal irrigation passageway 38 via a distal fluid delivery passageway 40. It is contemplated, however, that second irrigation lumen 34 may be in direct fluid communication with distal irrigation passageway 38 in certain embodiments of the invention.

Conversely, first irrigation lumen 32 is fluidly isolated from distal irrigation passageway 38, and second irrigation lumen 34 is fluidly isolated from proximal irrigation passageway 36. Thus, first irrigation lumen 32 provides a dedicated and independent proximal irrigation flow, while second irrigation lumen 34 provides a dedicated and independent distal irrigation flow.

Figure 8:
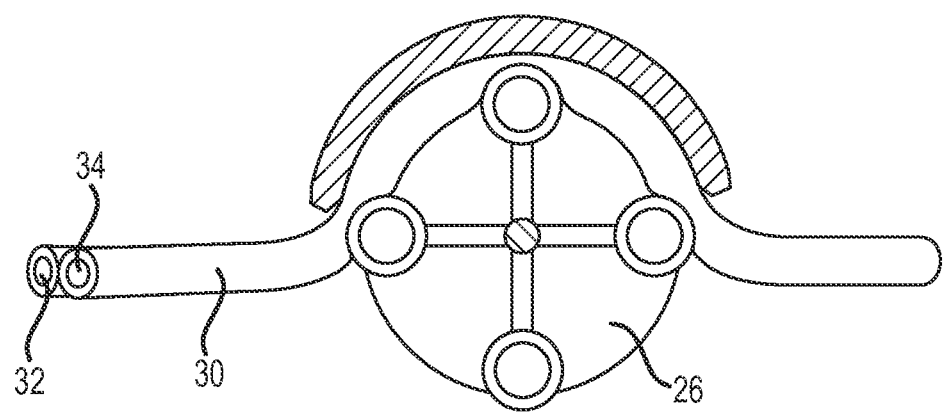
FIG. 8 depicts the interaction between a rolling pump and a multi-lumenal tubing.

Typically, both first fluid delivery tube 31 and second fluid delivery tube 33 will be connected to the same irrigation fluid source. It should be understood, however, that each fluid delivery tube may be connected to a dedicated irrigation fluid source without departing from the spirit and scope of the present teachings. In either case, however, pump 26 operates to pump an irrigation fluid from the irrigation fluid source, through the irrigation lumens, and out the irrigation passageways. FIG. 8 depicts the interaction between a rolling pump 26 and multi-lumenal tubing 30.

Figure 5:
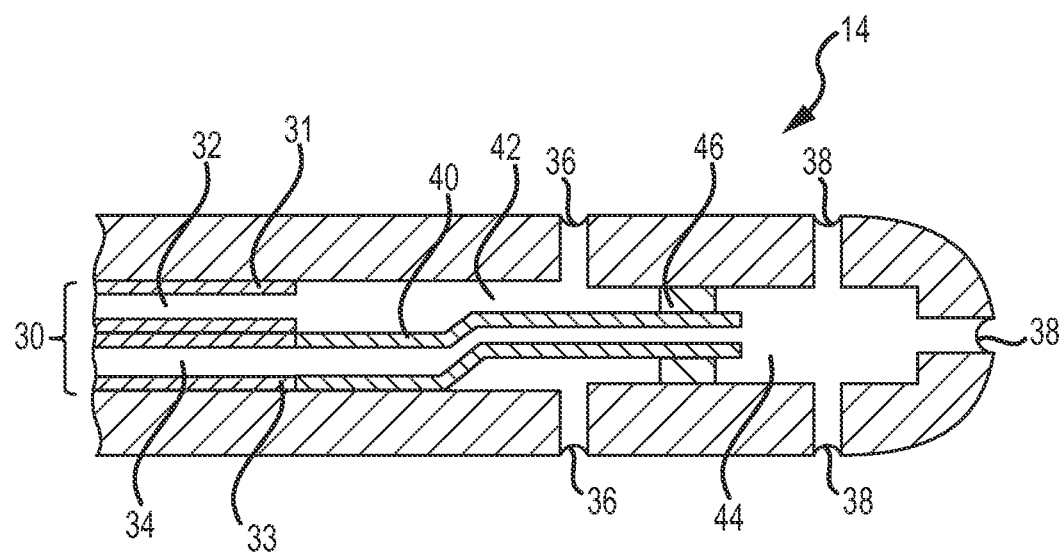
FIG. 5 is a longitudinal cross-sectional view of the distal end portion of a catheter body according to other aspects of the present invention.

FIG. 5 depicts a cut-away view depicting the interior of a second embodiment of distal end portion 14 of catheter body 12, which may also be employed in distal end region 100 of electrophysiology mapping catheter 102 (or any other irrigated catheter or similar device) to deliver dedicated proximal and distal irrigation flows. This embodiment of distal end portion 14 of catheter body 12 is somewhat similar to that depicted in FIG. 4, though the embodiment of the invention illustrated in FIG. 5 includes three distal irrigation passageways 38 rather than only a single distal irrigation passageway as shown in FIG. 4. In the embodiment of FIG. 5, however, first irrigation lumen 32 is in fluid communication with proximal irrigation passageways 36 via a proximal fluid manifold 42. Similarly, second irrigation lumen 34 is in fluid communication with distal irrigation passageways 38 via a distal fluid manifold 44. Proximal fluid manifold 42 is fluidly isolated from distal fluid manifold 44 via a fluid barrier 46.

Although several embodiments of this invention have been described above with a certain degree of particularity, those skilled in the art could make numerous alterations to the disclosed embodiments without departing from the spirit or scope of this invention. For example, though the present invention has been described in connection with a catheter that includes two sets of irrigation passageways (e.g., proximal and distal) supplied by a double lumen irrigation tube, it is contemplated that an irrigation tube having more than two irrigation lumens may be used to supply irrigation to a catheter having more than two sets of irrigation passageways (e.g., proximal, mid, and distal).

Similarly, the present invention may be employed to good advantage in both open irrigated and insulated irrigated arrangements.

It is also contemplated that the teachings herein may be readily adapted to deliver any fluids, including therapeutic substances such as chemicals, pharmaceuticals, and the like, without departing from the spirit and scope of the present invention. Likewise, the fluid characteristics (e.g., temperature, flow rate) may vary from one fluid source to another.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An apparatus, comprising:
    a catheter shaft having a proximal end portion and a distal end portion, the distal portion including a plurality of irrigation passageways;
    at least one electrode on the distal end portion of the catheter shaft; and
    a multi-lumenal fluid delivery tube extending from the proximal end portion of the catheter shaft and through the catheter shaft, wherein the multi-lumenal fluid delivery tube defines a plurality of separate fluid delivery lumens including a first fluid delivery lumen and a second fluid delivery lumen,
    wherein the first fluid delivery lumen is in fluid communication with a first subset of the plurality of irrigation passageways and fluidly isolated from a second subset of the plurality of irrigation passageways; and
    wherein the second fluid delivery lumen is in fluid communication with a third subset of the plurality of irrigation passageways and fluidly isolated from a fourth subset of the plurality of irrigation passageways.

2. The apparatus according to claim 1, wherein the first subset of the plurality of irrigation passageways is co-extensive with the fourth subset of the plurality of irrigation passageways and the second subset of the plurality of irrigation passageways is co-extensive with the third subset of the plurality of irrigation passageways.

3. The apparatus according to claim 1, further comprising:
    a first irrigation manifold in fluid communication with both the first fluid delivery lumen and the first subset of the plurality of irrigation passageways; and
    a second irrigation manifold in fluid communication with both the second fluid delivery lumen and the third subset of the plurality of irrigation passageways,
    wherein the first irrigation manifold is fluidly isolated from the second irrigation manifold.

4. The apparatus according to claim 1, further comprising:
    at least one irrigation fluid supply in fluid communication with the first fluid delivery lumen and the second fluid delivery lumen; and
    a pump operable to pump an irrigation fluid from the at least one irrigation fluid supply, through the first fluid delivery lumen and the second fluid delivery lumen, and out the plurality of irrigation passageways.

5. The apparatus according to claim 1, further comprising a generator operably coupled to the at least one electrode.

6. The apparatus according to claim 1, wherein the multi-lumenal fluid delivery tube has a flattened axial cross-sectional shape.

7. The apparatus according to claim 1, wherein each of the plurality of separate fluid delivery lumens defined by the multi-lumenal fluid delivery tube has a substantially identical axial cross-sectional area.

* * * * *